(12) United States Patent
Svensson et al.

(10) Patent No.: US 8,939,929 B2
(45) Date of Patent: Jan. 27, 2015

(54) INFUSION CONTROL DEVICE

(76) Inventors: Fredrik Svensson, Järfälla (SE);
Lennart Lood, Sollentuna (SE); Martin Dunér, Spånga (SE)

(*) Notice: Subject to any disclaimer, the term of this patent is extended or adjusted under 35 U.S.C. 154(b) by 0 days.

(21) Appl. No.: 13/519,904

(22) PCT Filed: Dec. 17, 2010

(86) PCT No.: PCT/SE2010/000305
§ 371 (c)(1),
(2), (4) Date: Jun. 29, 2012

(87) PCT Pub. No.: WO2011/081585
PCT Pub. Date: Jul. 7, 2011

(65) Prior Publication Data
US 2012/0283632 A1    Nov. 8, 2012

(30) Foreign Application Priority Data

Dec. 30, 2009  (SE) .................................. 0901621-3

(51) Int. Cl.
*A61M 31/00*  (2006.01)
*A61M 5/168*  (2006.01)
*A61M 5/14*  (2006.01)

(52) U.S. Cl.
CPC .......... *A61M 5/1411* (2013.01); *A61M 5/1689* (2013.01)
USPC ......................................................... 604/67

(58) Field of Classification Search
CPC ................... A61M 5/1689; A61M 2205/3393; A61M 5/16895; A61M 5/1411; A61M 5/16831; A61M 5/172; G01G 17/04; G01G 1/7044
USPC .................................................... 604/67, 131
See application file for complete search history.

(56) References Cited

U.S. PATENT DOCUMENTS

| 4,038,982 | A | * | 8/1977 | Burke et al. ..................... 604/65 |
| 4,321,461 | A | | 3/1982 | Walter, Jr. et al. |
| RE32,294 | E | * | 11/1986 | Knute ............................. 604/253 |
| 4,775,368 | A | * | 10/1988 | Iwatschenko ................. 604/253 |
| 5,088,990 | A | | 2/1992 | Hivale et al. |

(Continued)

FOREIGN PATENT DOCUMENTS

| CN | 201316463 Y | 9/2009 |
| CN | 101732783 A | 6/2010 |

(Continued)

OTHER PUBLICATIONS

Extended European Search Report dated Aug. 16, 2013 from corresponding EP 10841367.5-1662.

*Primary Examiner* — Nicholas Lucchesi
*Assistant Examiner* — Diva K Chander
(74) *Attorney, Agent, or Firm* — Porter Wright Morris & Arthur LLP

(57) ABSTRACT

The present invention relates to an infusion control device designed to secure the infusion control device to a drip chamber attached to an infusion tube. The infusion control device comprises a light indicator and a microprocessor. The microprocessor determines the amount of fluid in an infusion bottle providing fluid to the transparent drip chamber, and provides instructions to the light indicator to illuminate the infusion bottle when the amount of fluid in the infusion bottle is less than a predetermined first limit.

12 Claims, 2 Drawing Sheets

(56) References Cited

U.S. PATENT DOCUMENTS

| | | | |
|---|---|---|---|
| 5,152,424 A * | 10/1992 | Weinreb et al. | 222/1 |
| 5,938,643 A * | 8/1999 | Lerner | 604/253 |
| 6,571,644 B2 * | 6/2003 | Handschuck | 73/861.41 |
| 7,307,739 B2 * | 12/2007 | Kamiya et al. | 356/627 |
| 7,327,273 B2 * | 2/2008 | Hung et al. | 340/619 |
| 8,540,698 B2 * | 9/2013 | Spohn et al. | 604/533 |
| 2006/0030822 A1 | 2/2006 | Hung et al. | |
| 2012/0283632 A1 * | 11/2012 | Svensson et al. | 604/67 |

FOREIGN PATENT DOCUMENTS

| | | |
|---|---|---|
| EP | 0718001 A2 | 6/1996 |
| GB | 1441663 A | 7/1976 |
| GB | 2314162 A | 12/1997 |
| GB | 2406520 A | 4/2005 |

* cited by examiner

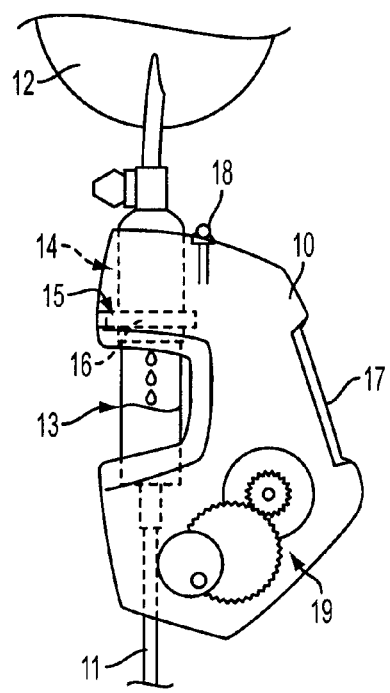
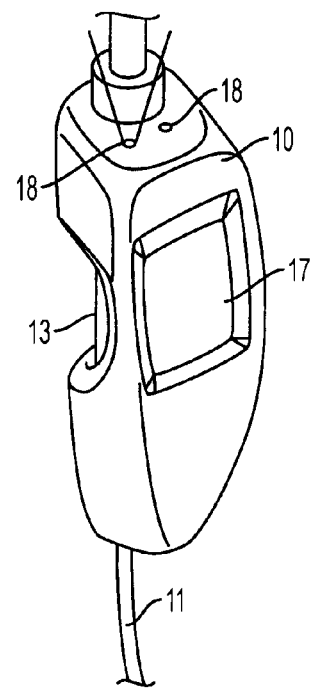
FIG. 1A  FIG. 1B
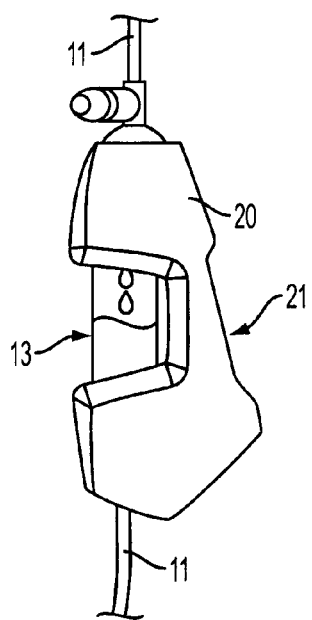
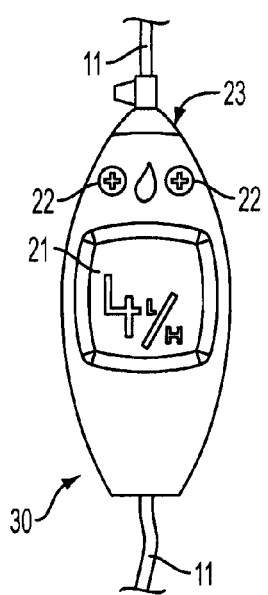
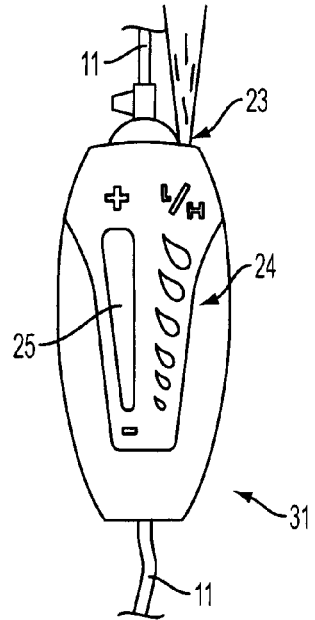
FIG. 2A  FIG. 2B  FIG. 3

INFUSION CONTROL DEVICE

RELATED APPLICATION

The present application is a 371 of PCT/SE2010/000305 filed Dec. 17, 2010.

TECHNICAL FIELD

The present invention relates to an infusion control device designed to monitor infusion as defined in independent claim 1.

BACKGROUND

Today, infusion of fluids (which includes any type of liquid with or without medicaments in liquid form) is mainly controlled by trained medical personnel, such as nurses, that manually set the appropriate dosage by counting drops in a transparent drip chamber and adjusting a regulating valve, which are attached to an infusion tube that connects an infusion bottle with a patient, until the correct flow of fluid is obtained.

The infusion needs to be continuously monitored to ensure that correct dosage is administered to the patient, which requires the medical personnel to regularly check the amount of fluid left in the infusion bottle, and also to check that the flow of fluids is unchanged, e.g. a reduced flow when the infusion tube is squeezed, or an increased flow if the needle inserted into the patient is withdrawn. These tasks are time consuming and as a result, the time interval between each check may vary dependent on the amount of personnel on duty. Consequently, there is a major risk that the wrong dosage of a fluid is administered to a patient between checks, which may cause the patient harm.

In the published utility model CN 201316463, an infusion prompting device is disclosed having a detecting sensor 3 which prompts a flashing light 6 to emit flash lamp light when only a small amount of infuse fluid is left in an infusion bottle. A problem with the described infusion prompting device is that light is rather small and situated on one side of the infusion prompting device. It may be difficult to see the light in case the flashing light is turned away from the nurse making the round, or something (e.g. curtains, ward partitioning walls, etc.) is blocking the view for the nurse.

In U.S. Pat. No. 5,938,643 a drop monitoring unit for infusion sets is disclosed having light indicators in combination with a buzzer which are used to indicate deviation from normal operation. However, the light indicators are rather small and it is therefore difficult to catch the attention of a nurse making the rounds. The combination with the buzzer helps the nurse to identify any problem, but will also disturb the patients nearby.

Thus, there is a need to provide an infusion control device that may further simplify the monitoring tasks for medical personnel.

SUMMARY OF THE INVENTION

An object with the present invention is to provide an infusion control device, which may be secured to a standard infusion tube, provided with an improved alarm indicator compared to prior art devices.

This object is achieved by an infusion control device comprising a securing unit configured to secure the infusion control device to a transparent drip chamber attached to an infusion tube, a light indicator configured to illuminate an object, and a microprocessor. The microprocessor is configured to determine the amount of fluid in an infusion bottle providing fluid to the transparent drip chamber, and configured to provide instructions to the light indicator to illuminate the object when the amount of fluid in the infusion bottle is less than a predetermined first limit.

An advantage with the present invention is that medical personnel may only be alerted by illumination by a light source when action needs to be taken.

Another advantage with the present invention is that medical personnel, during night rounds, do not have to turn on the light in a hospital ward to check the infusion and thereby unnecessarily disturb the patients in the ward.

Further objects and advantages may be found by a skilled person in the art from the detailed description.

BRIEF DESCRIPTION OF DRAWINGS

The invention will be described in connection with the following drawings that are provided as non-limited examples, in which:

FIG. 1a shows a side view of a first embodiment of an infusion control device according to the invention secured to a standard infusion tube attached to an infusion bottle.

FIG. 1b shows a perspective view of the infusion control device in FIG. 1a.

FIG. 2a shows a side view of a second embodiment of an infusion control device according to the invention secured to a standard infusion tube.

FIG. 2b shows a front view of a first version of the infusion control device in FIG. 2a.

FIG. 3 shows a front view of an alternative version of the infusion control device in FIG. 2a.

DETAILED DESCRIPTION

Figure 4:
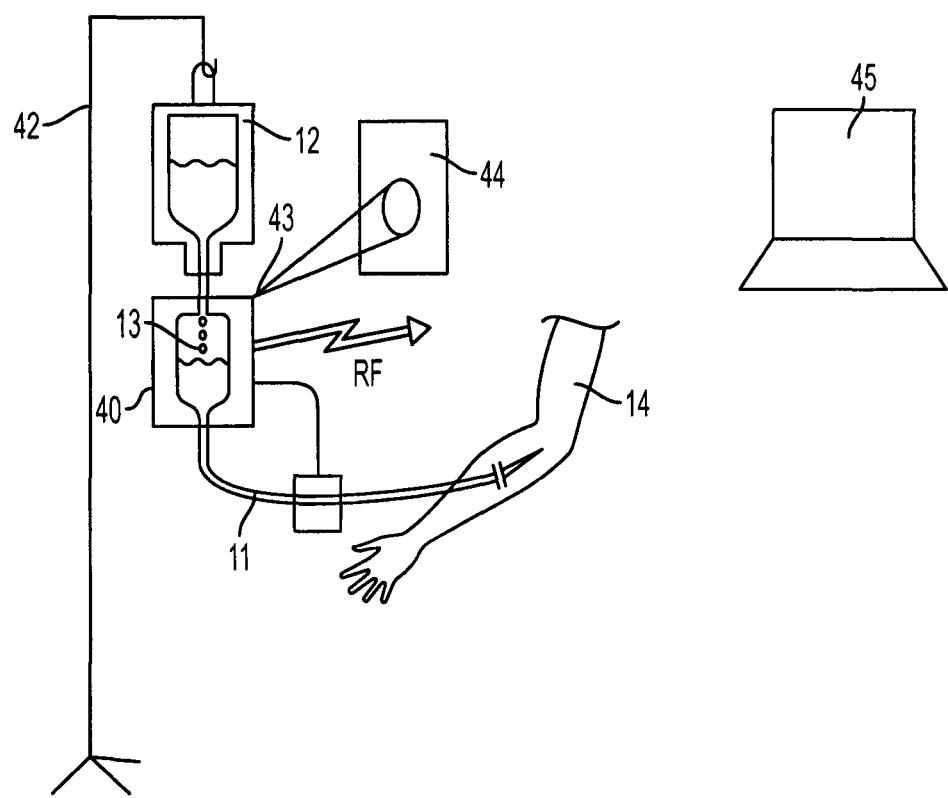
FIG. 4 shows a third embodiment of an infusion control device according to the invention secured to a standard infusion tube attached to an infusion bottle and inserted into a patient.

The basic concept of the invention is a soundless indication to catch the attention of medical personnel when work needs to be performed on an infusion attached to a specific patient, e.g. change the infusion bottle when empty, correct the flow of fluid if deviating from a desired flow rate, etc. The soundless indication is preferably light from a light indicator, such as a light emitting diode. Different colours may be used to indicate different actions needed. The light is preferably directed at a specific object to immediately catch the attention when a nurse makes the round and looks into a ward at a hospital. The object may be a surface adjacent to the infusion control device, e.g. wall, ceiling, curtain, screen, etc., but most preferably the object is the infusion bottle. In order to enhance the indication of light, it may be necessary to modify the material of the infusion bottle, dependent on the type of fluid contained in the infusion bottle, to re-emit absorbed light.

The invention provides a means to monitor infusion and give a silent alarm if the infusion bottle is empty, the flow of fluid into the patient is not correct, the infusion tube is blocked (e.g. by stop in the needle which is inserted into the patient), and also to indicate when an infusion is completed (regardless if the bottle is empty or not).

FIG. 1a shows a side view, and FIG. 1b shows a perspective view, of a first embodiment of an infusion control device 10 secured to a standard infusion tube 11 attached to an infusion bottle 12. A drip chamber 13, preferably transparent, is attached to the infusion tube 11 and the infusion control device 10 is secured to the drip chamber 13 using a securing unit, which in this embodiment is implemented as a through-hole 14 provided with an indentation 15. The drip chamber is provided with a rim 16 (or the like) which makes it impossible for the drip chamber 13 to pass completely through the hole 14 whereby the infusion control device 10 may rest on the rim 16 when the infusion tube 11 (with the drip chamber 13) is inserted through the hole 14.

An example of alternative solution to the securing unit is a recess along the rear side of the infusion control device adapted to fit the infusion tube 11 and the drip chamber 13. Another example is a griping section that is designed to clamp the infusion control device to the drip chamber 13. Other solutions are readily available to a skilled person in the art.

The infusion control device is also provided with two light emitting diodes (LEDs) 18 arranged to a top surface of the infusion control device 10, and a microprocessor (not shown). The microprocessor determines the amount of fluid in the infusion bottle 12 providing fluid to the transparent drip chamber 13, and also provides instructions to the light indicator, i.e. energize a first of the LEDs to illuminate the infusion bottle 12 when the amount of fluid in the infusion bottle is less than a predetermined first limit, which is set in the infusion control device.

In this embodiment, the infusion control device 10 is further provided with a touch display 17, which operates as input unit as well as output unit, arranged on a front side. The input unit is configured to receive information of a desired flow of fluid through the infusion tube 11 from medical personnel, and the microprocessor controls the flow of fluid through the infusion tube 11 in response to the desired flow of fluid, and provides instructions to a second of the LEDs to illuminate the infusion bottle 12 when the flow of fluid deviates from the desired flow of fluid more than a predetermined second limit. It is of course possible to use one LED, but it may be advantageous to use different colours to indicate different actions needed, such as replacing an empty bottle with a new one In order to determine the flow of fluid, the infusion control device 10 is also provided with a drop counter (not shown) preferably in the form of an optic sensor, e.g. photo diode, mounted close to the transparent drip chamber 13, as obvious for a skilled person in the art. Furthermore, in order to be able to control the flow of fluid through the infusion tube 11, the infusion control device 10 is further provided with a flow controller, preferably a motor controlled cam disk 19, and the microprocessor provides instructions to the flow controller to control the flow of fluid through the infusion tube 11 in response to the desired flow of fluid entered via the touch display 17.

It should also be noted that a part of the drip chamber 13 is accessible at the rear of the infusion control device 10, which makes it possible to squeeze the soft part of the drip chamber with one's fingers to start the infusion process by pumping.

FIG. 2a shows a side view, and FIG. 2b shows a front view of a first version, of a second embodiment of an infusion control device 20 secured to a drip chamber 13 and a standard infusion tube 11.

In this embodiment, a simplified version of the infusion control device from FIGS. 1a and 1b is described. A drop counter is connected to a microprocessor to determine the amount of fluid left in the infusion bottle, as well as providing information regarding the flow rate of fluid through the infusion tube 11. On the first version of the front side 30, the flow rate is presented on a display 21 and a set value is entered using buttons 22. The actual flow of fluid may be regulated by a manually controlled valve arranged downstream of the drip chamber 13.

One LED is arranged on the top side of the infusion control device 20 to illuminate the infusion bottle (not shown) or an adjacent surface, such as a curtain, wall, ceiling, etc.

FIG. 3 shows a second alternative version 31 of a front view of the infusion control device in FIG. 2a. The flow rate is presented on a scale to the right 24 and the desired flow of fluid is entered using a touch slider 25.

The LED 23 is arranged at the same position for both versions and is activated by the microprocessor if the amount of fluid left in the infusion bottle is below the first predetermined limit or the flow of fluid deviates from the desired flow of fluid (which is set by the buttons 22 in FIG. 2b or by the touch slider 25 in FIG. 3) more than a predetermined second limit.

FIG. 4 shows a third embodiment of an infusion control device 40 according to the invention secured to a standard infusion tube 11 attached to an infusion bottle 12 and inserted into the arm of a patient 41.

The infusion bottle is hanging from a support 42 and the infusion control device 40 is secured to the drip chamber 13, as previously discussed. A light indicator, such as an LED 43, is arranged in such a way that an adjacent surface 44 is illuminated when the attention of medical personnel is required. It is also possible to include other types of silent indicators, such as radio communication (RF) to a central monitoring unit 45, from which medical personnel may monitor patients and only need to check the infusion whenever an alarm is presented on the display.

An external flow controller 46 is connected to the infusion control device 40 to regulate the flow in response to the inputted desired flow of fluid.

In all the above described embodiments it is possible to implement flows that vary over time, e.g. slow from the beginning and increasing towards the en, without having to readjust the flow rate manually if an automatic flow controller is provided.

The light emitted from the light indicator is preferably a monochromatic light, and as mentioned above different colours may be used to indicate different actions required by the medical staff.

The invention claimed is:

1. An infusion control device, comprising:
    a securing unit configured to secure said infusion control device to a transparent drip chamber attached to an infusion tube,
    a light indicator arranged on a top side of said infusion control device and configured to illuminate an infusion bottle providing fluid to the transparent drip chamber, and
    a microprocessor configured to:
        determine the amount of fluid in said infusion bottle providing fluid to the transparent drip chamber, and
        provide instructions to said light indicator to illuminate said infusion bottle when said amount of fluid in said infusion bottle is less than a predetermined first limit.

2. The infusion control device according to claim 1, further comprising an input unit configured to receive information of a desired flow of fluid through said infusion tube,
    wherein said microprocessor is further configured to:
        control a flow of fluid through said infusion tube in response to the desired flow of fluid, and
        provide instructions to said light indicator to illuminate said infusion bottle when said flow of fluid deviates from said desired flow of fluid more than a predetermined second limit.

3. The infusion control device according to claim 2, further comprising a drop counter to determine said flow of fluid by detecting a speed of dropping fluid in said transparent drip chamber.

4. The infusion control device according to claim 2, wherein said drop counter is an optic sensor.

5. The infusion control device according to claim 2, further comprising a flow controller, wherein said microprocessor is configured to provide instructions to said flow controller to control said flow of fluid through said infusion tube.

6. The infusion control device according to claim 5, wherein said flow controller is a motor controlled cam disk.

7. The infusion control device according to claim 2, wherein said input unit comprises at least one of a touch display, buttons and a numeric unit.

8. The infusion control device according to claim 1, wherein said securing unit is provided with an indentation configured to hold a circumferential rim of said transparent drip chamber.

9. The infusion control device according to claim 8, wherein said securing unit is a through-hole configured to receive and secure said infusion tube and said transparent drip chamber.

10. The infusion control device according to claim 8, wherein said securing unit is a recess configured to receive and secure said infusion tube and said transparent drip chamber.

11. The infusion control device according claim 1, wherein said light indicator is a light emitting diode.

12. The infusion control device according to claim 1, wherein a material of said infusion bottle is configured to re-emit absorbed light from said light indicator.

* * * * *